United States Patent [19]

Angerbauer et al.

[11] Patent Number: 5,861,385
[45] Date of Patent: Jan. 19, 1999

[54] SUBSTITUTED TRIOLS

[75] Inventors: Rolf Angerbauer; Peter Fey; Walter Hübsch, all of Wuppertal, Germany; Thomas Philipps, deceased, late of Eupen, Belgium, by Beate Martha Fatzaun, Charlotte Elisabeth Philipps and Maxim Philipps, Heirs.; Hilmar Bischoff, Wuppertal, Germany; Hans-Peter Krause, Schwelm, Germany; Jörg Petersen von Gehr, Bochum, Germany; Delf Schmidt, Wuppertal, Germany

[73] Assignee: Bayer Aktiengesellschaft, Leverkusen, Germany

[21] Appl. No.: 464,682

[22] PCT Filed: Dec. 8, 1993

[86] PCT No.: PCT/EP93/03459

§ 371 Date: Aug. 8, 1995

§ 102(e) Date: Aug. 8, 1995

[87] PCT Pub. No.: WO94/14807

PCT Pub. Date: Jul. 7, 1994

[30] Foreign Application Priority Data

Dec. 21, 1992 [DE] Germany .......................... 42 43 279.0

[51] Int. Cl.[6] .......................... C07D 309/10; C07C 47/52; C07C 67/02; C07F 9/02

[52] U.S. Cl. .......................... 514/140; 514/141; 514/142; 514/451; 514/553; 514/576; 514/577; 514/675; 514/678; 514/682; 514/699; 514/700; 514/701; 549/417; 558/117; 560/256; 562/23

[58] Field of Search .......................... 549/417; 514/451, 514/140, 141, 142, 576, 577, 553, 675, 678, 682, 699, 700, 701; 558/177; 560/256; 562/23; 568/425, 440, 445, 808, 809, 811, 823

[56] References Cited

U.S. PATENT DOCUMENTS

| | | | |
|---|---|---|---|
| 4,231,938 | 11/1980 | Monaghan et al. | 260/343.5 |
| 4,294,926 | 10/1981 | Monaghan et al. | 435/125 |
| 4,440,927 | 4/1984 | Prugh | 549/292 |
| 4,686,237 | 8/1987 | Anderson | 514/532 |
| 4,925,852 | 5/1990 | Kesseler et al. | 514/333 |
| 4,997,837 | 3/1991 | Chucholowski et al. | 514/256 |
| 5,004,747 | 4/1991 | Ashton et al. | 514/309 |
| 5,072,002 | 12/1991 | Clive et al. | 549/214 |
| 5,177,080 | 1/1993 | Angerbauer et al. | 514/277 |
| 5,196,940 | 3/1993 | Sato | 358/228 |
| 5,401,746 | 3/1995 | Angerbauer et al. | 514/277 |

FOREIGN PATENT DOCUMENTS

| | | |
|---|---|---|
| 0463456 | 1/1992 | European Pat. Off. . |
| 0465970 | 1/1992 | European Pat. Off. . |
| 0402131 | 10/1993 | European Pat. Off. . |
| WO-A-8402131 | 6/1984 | WIPO . |

OTHER PUBLICATIONS

Prugh et al., Synthesis and Utilization of the Chiral Synthon., J. Org. Chem., 51, pp. 648–657, 1986.
Prugh et al., Utilization of the Chiral Synthon., Tetrahedron Letters, vol. 26, No. 25, pp. 2947–2950, 1985.
Lee et al., Structural Modification of Mevinolin, J. Org. Chem., 47, pp. 4750–4757, 1982.
I.W. Duncan, et al., Journal of Chromatography, vol. 162, pp. 281–292, (1979).
Journal of Midicinal Chemistry, vol. 36., No. 23, 1993, Washington, US, pp. 3646–3657.

*Primary Examiner*—Mukund J. Shah
*Assistant Examiner*—Deepak R. Rao
*Attorney, Agent, or Firm*—Sprung Kramer Schaefer & Briscoe

[57] ABSTRACT

Substituted triols are prepared by reducing appropriately substituted carboxylic esters. The substituted triols can be used as active substances in medicaments.

8 Claims, No Drawings

SUBSTITUTED TRIOLS

This application is a 371 of PCT/EP93/03459, filed Dec. 8, 1993.

The invention relates to substituted triols, to a process for their preparation, and to their use in medicaments.

It has been disclosed that lactone derivatives isolated from fungal cultures are inhibitors of 3-hydroxy-3-methyl-glutayl coenzyme A reductase (HMG-CoA reductase) [mevinolin, EP 22 478; U.S. Pat. No. 4,231,938].

It has additionally been disclosed that pyridine-substituted dihydroxyheptenoic acids are inhibitors of HMG-CoA reductase [EP 325 130; EP 307 342; EP 306 929].

The present invention relates to substituted triols of the general formula (I)

in which

D represents a hetero- or carbocyclic radical of the formula

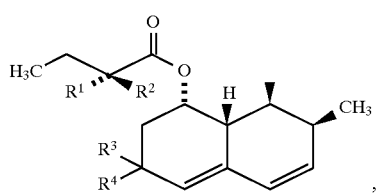

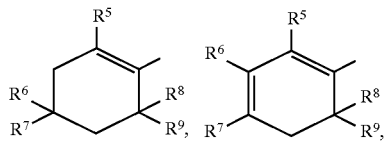

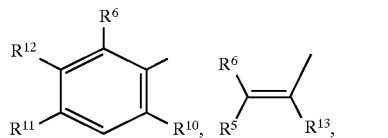

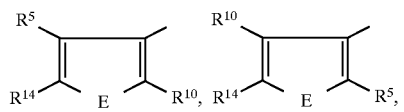

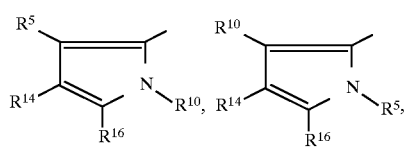

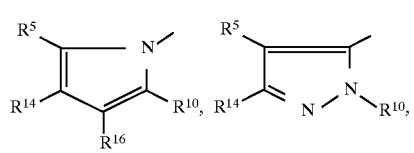

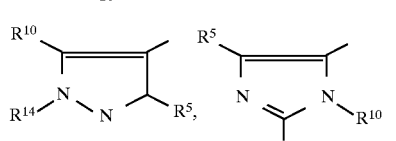

-continued

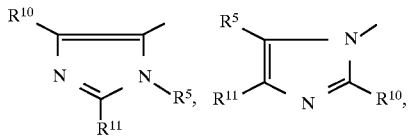

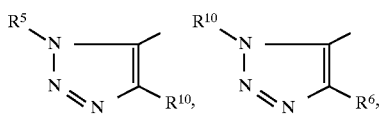

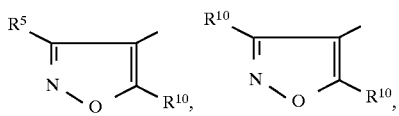

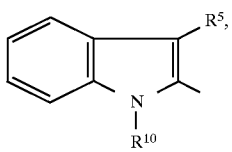

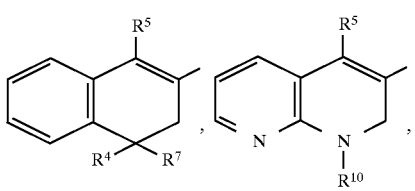

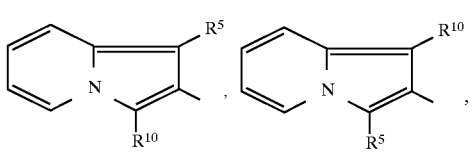

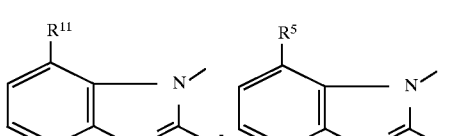

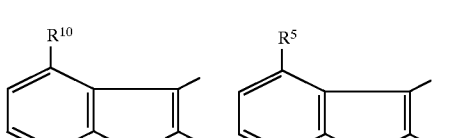

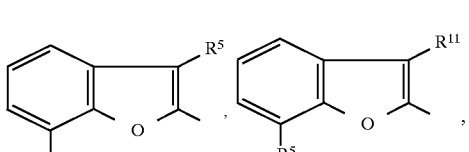

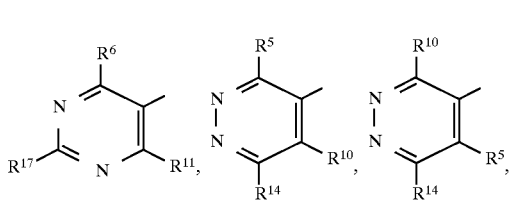

-continued

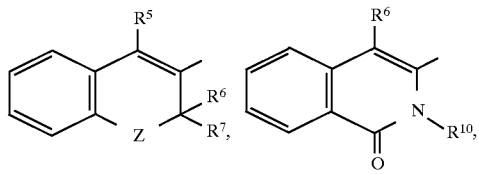
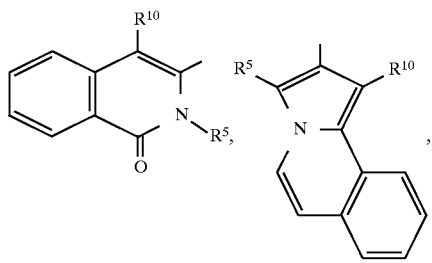
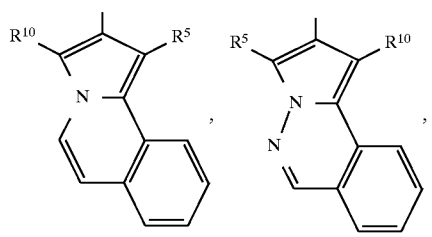
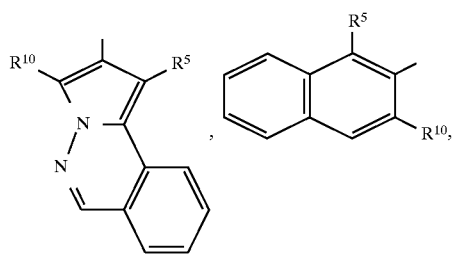
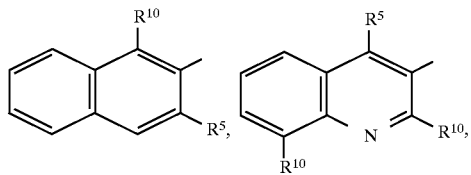
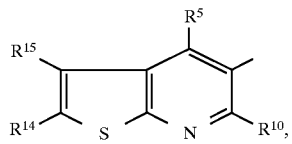
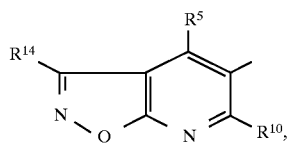
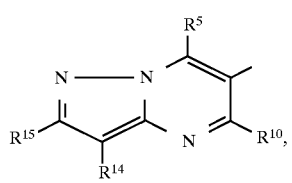

-continued

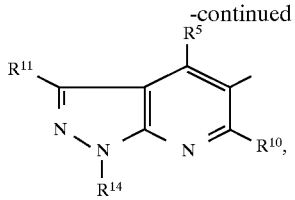
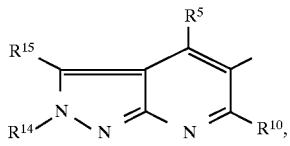
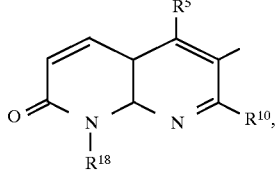
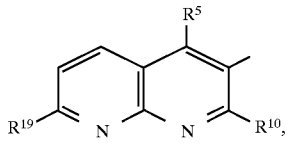
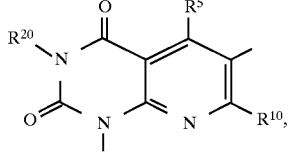
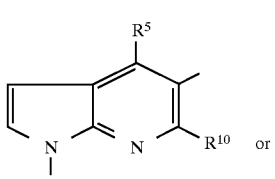
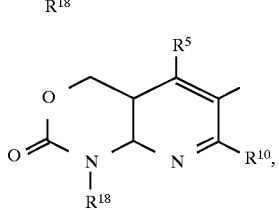

wherein
$R^1$, $R^2$, $R^3$ and $R^4$ are identical or different and denote hydrogen or methyl, or $R^4$ denotes hydroxyl, $R^5$ denotes phenyl which is optionally substituted up to 2 times by identical or different substituents from the group consisting of halogen, trifluoromethyl and straight-chain or branched alkyl having up to 8 carbon atoms, $R^6$, $R^7$, $R^8$ and $R^9$ are identical or different and denote hydrogen, straight-chain or branched alkyl having up to 8 carbon atoms or cycloalkyl having 3 to 6 carbon atoms, or in each case $R^6$ and $R^7$ and/or $R^8$ and $R^9$ each together form a saturated or partially saturated carbocycle having 3 to 6 carbon atoms $R^{10}$ denotes cycloalkyl having 3 to 7 carbon atoms, or denotes straight-chain or branched alkyl having up to 8 carbon atoms, $R^{11}$ has the abovementioned meaning of $R^{10}$ and is identical to or different from this or denotes hydrogen or phenyl, $R^{12}$ denotes hydrogen or straight-chain or branched alkyl having up to 8 carbon atoms, which is optionally substituted by hydroxyl or straight-chain or branched alkoxy having up to 6 carbon atoms, or by benzyloxy which for its part can be substituted by halogen or trifluoromethyl or by straight-chain or branched alkyl having up to 4 carbon atoms, $R^{13}$ is hydrogen or straight-chain or branched alkyl having up to 8 carbon atoms or a radical of the formula

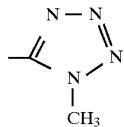

$R^{14}$ and $R^{15}$ are identical or different and denote hydrogen or straight-chain or branched alkyl having up to 8 carbon atoms, or denote phenyl or benzyl, each of which is optionally substituted up to 2 times by identical or different substituents from the group consisting of halogen, trifluoromethyl, cyano and nitro or by straight-chain or branched alkyl having up to 6 carbon atoms, $R^{16}$ has the abovementioned meaning of $R^{14}$ and $R^{15}$ and is identical to or different from this, or denotes pyridyl or a radical of the formula —CO—NH-L, wherein L denotes phenyl which is optionally substituted by halogen or trifluoromethyl, $R^{17}$ likewise has the abovementioned meanings of $R^{14}$ and $R^{15}$ and is identical to or different from these, or denotes a radical of the formula —NMM', wherein M and M' are identical or different and denote hydrogen or straight-chain or branched alkyl having up to 6 carbon atoms or benzyl, $R^{18}$ denotes hydrogen or straight-chain or branched alkenyl, alkinyl or alkyl in each case having up to 8 carbon atoms, the latter optionally being substituted by cyano or phenyl which for its part can be substituted by halogen or trifluoromethyl or by straight-chain or branched alkyl having up to 6 carbon atoms, $R^{19}$ denotes straight-chain or branched alkoxy having up to 8 carbon atoms, benzoyl or the group —NMM', wherein M and M' have the abovementioned meaning, $R^{20}$ denotes hydrogen, straight-chain or branched alkyl having up to 8 carbon atoms or benzoyl, E denotes an oxygen or sulphur atom, or a group of the formula —N—$R^{10}$, Z denotes a sulphur or oxygen atom or the —$CH_2$— group and R represents a radical of the formula

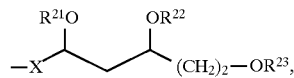

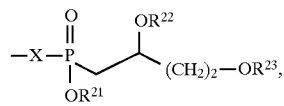

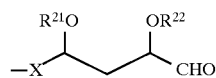

or

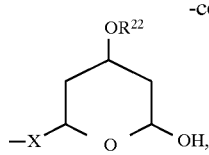

-continued wherein

X denotes the group —$CH_2$—$CH_2$—, —CH=CH— or —C≡C—, $R^{21}$, $R^{22}$ and $R^{23}$ are identical or different and denote a hydroxyl protective group, hydrogen or a radical of the formula —CO—$R^{24}$ or —$CO_2$—$R^{25}$, wherein $R^{24}$ and $R^{25}$ are identical or different and denote hydrogen or straight-chain or branched alkyl having up to 8 carbon atoms or phenyl, or $R^{21}$ and $R^{22}$ together form a radical of the formula

In the context of the present invention, physiologically acceptable salts are preferred. Physiologically acceptable salts of the Quinolylmethoxyphenyl-acetic acid amides can be salts of the substances according to the invention with mineral acids, carboxyl acids or sulphonic acids. Particularly preferred salts are e.g. those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Depending on the side chains listed under R, the compounds according to the invention in each case have 1 or 2 asymmetric carbon atoms, to which the radicals —$OR^{21}$ and —$OR^{22}$ are bonded. They can therefore exist in various stereochemical forms.

The invention relates both to the individual isomers and to their mixtures. Depending on the relative position of the radicals —$OR^{21}$/—$OR^{22}$, the substances according to the invention can thus be present in the erythro configuration or in threo configuration. This can be illustrated by way of example:

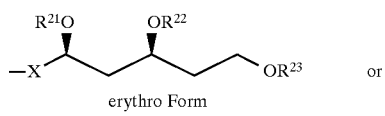
erythro Form

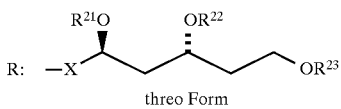
threo Form

In turn, two enantiomers both of the substances in the threo and in the erythro configuration in each case exist.

Moreover, the substances according to the invention can be present in the E configuration or the Z configuration on account of the double bond (X=—CH=CH—). Those compounds are preferred which have the E configuration.

The aldehydes in each case are additionally in equilibrium with the corresponding pyrans

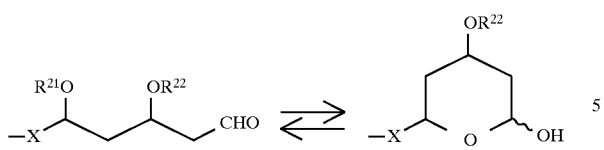
Preferred compounds of the general formula (I) are those in which
D represents a hetero- or carbocyclic radical of the formula
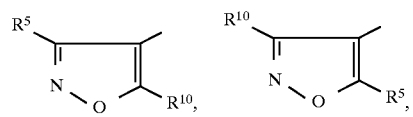
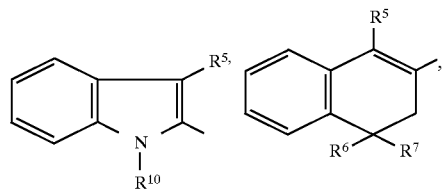
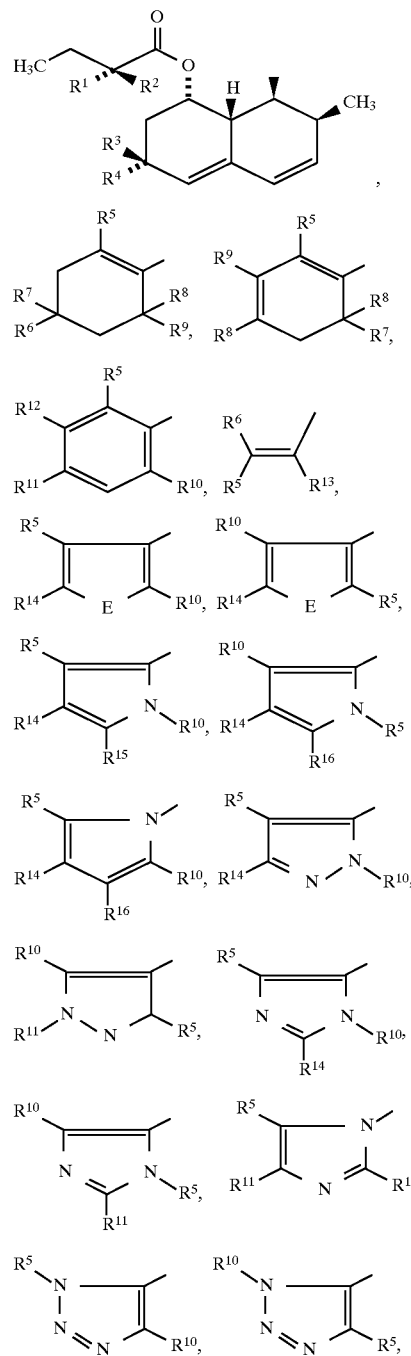
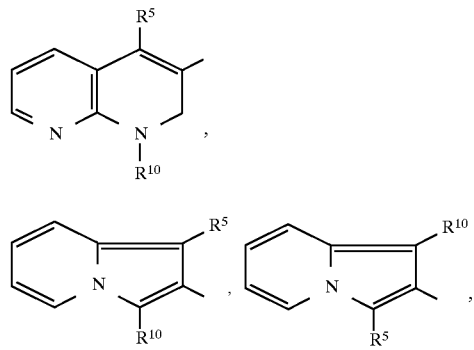
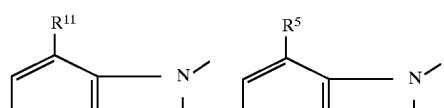
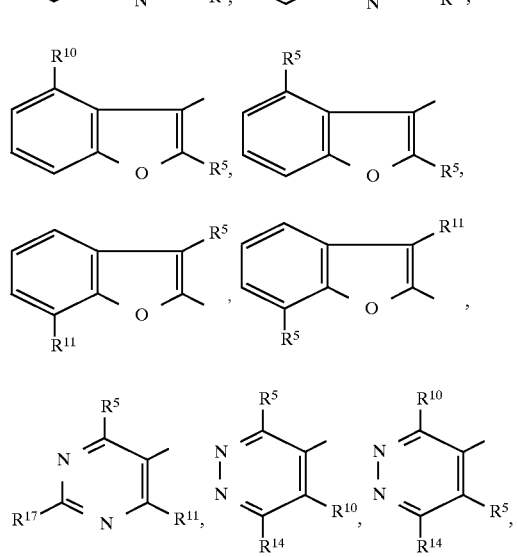
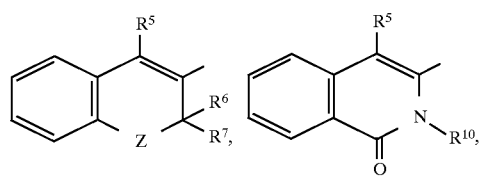

-continued

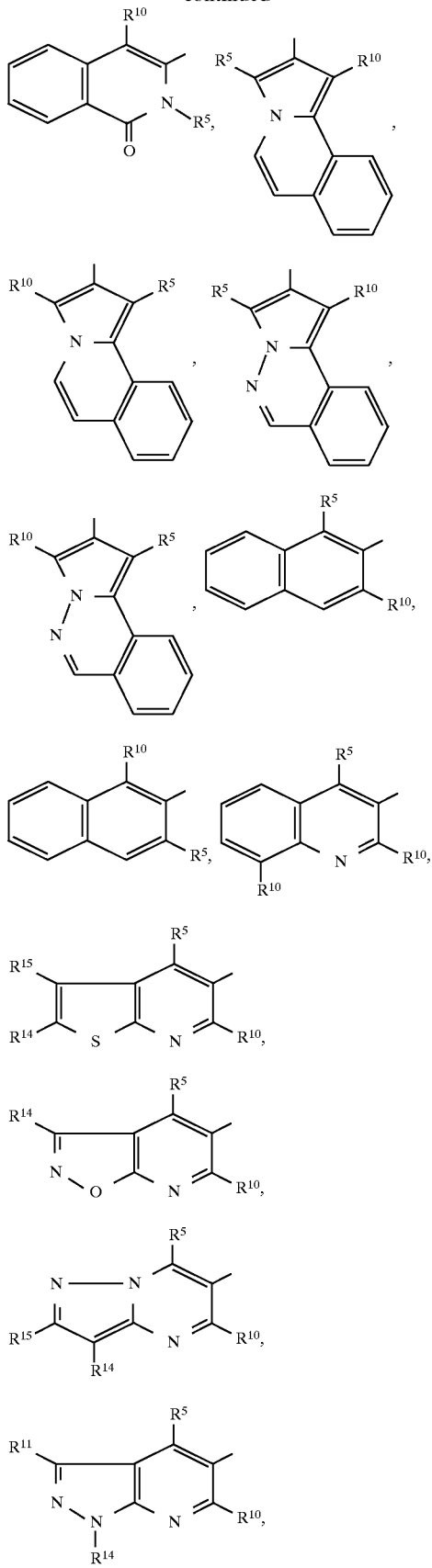
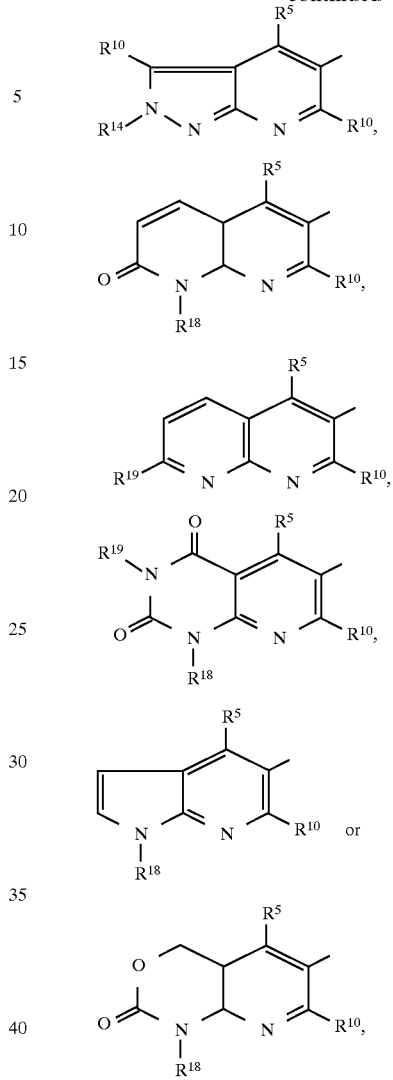

wherein
R¹, R², R³ and R⁴ are identical or different and denote hydrogen or methyl, or R⁴ denotes hydroxyl,
R⁵ denotes phenyl which is optionally substituted up to 2 times by identical or different substituents from the group consisting of fluorine, chlorine, bromine and trifluoromethyl or by straight-chain or branched alkyl having up to 6 carbon atoms,
R⁶, R⁷, R⁸ and R⁹ are identical or different and denote hydrogen or straight-chain or branched alkyl having up to 6 carbon atoms or cyclopropyl, cyclopentyl or cyclohexyl, or in each case R⁶ and R⁷ and/or R⁸ and R⁹ together form a cyclopropyl, cyclopentyl or cyclohexyl ring and/or R⁸ and R⁹ together form a cyclopentenyl or cyclohexenyl ring,
R¹⁰ denotes cyclopropyl, cyclopentyl or cyclohexyl, or denotes straight-chain or branched alkyl having up to 6 carbon atoms,
R¹¹ has the abovementioned meaning of R¹⁰ and is identical to or different from this or denotes hydrogen,
R¹² denotes hydrogen or straight-chain or branched alkyl having up to 6 carbon atoms, which is optionally substituted by hydroxyl or straight-chain or branched alkoxy having up to 4 carbon atoms, or by benzoyl which for its part can be substituted by fluorine, chlorine, bromine, trifluoromethyl or methyl, $R^{13}$ denotes straight-chain or branched alkyl having up to 6 carbon atoms or a radical of the formula

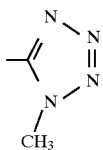

$R^{14}$ and $R^{15}$ are identical or different and denote hydrogen or straight-chain or branched alkyl having up to 6 carbon atoms, or denote phenyl or benzyl, each of which is optionally substituted by fluorine, chlorine, bromine, trifluoromethyl, cyano or nitro or by straight-chain or branched alkyl having up to 4 carbon atoms, $R^{16}$ has the abovementioned meaning of $R^{14}$ and $R^{15}$ and is identical to or different from this, or denotes pyridyl or a radical of the formula —CO—NH-L, wherein
L denotes phenyl which is optionally substituted by fluorine, chlorine, bromine or trifluoromethyl, $R^{17}$ likewise has the abovementioned meanings of $R^{14}$ and $R^{15}$ and is identical to or different from these, or denotes a radical of the formula —NMM', wherein
M and M' are identical or different and denote hydrogen or straight-chain or branched alkyl having up to 4 carbon atoms or benzyl, $R^{18}$ denotes hydrogen or straight-chain or branched alkenyl, alkinyl or alkyl in each case having up to 6 carbon atoms, the latter being substituted by cyano or phenyl which for its part can be substituted by fluorine, chlorine, bromine or trifluoromethyl or by straight-chain or branched alkyl having up to 4 carbon atoms, $R^{19}$ denotes straight-chain or branched alkoxy having up to 6 carbon atoms, benzoyl or the group —NMM', wherein
M and M' have the abovementioned meaning, $R^{20}$ denotes hydrogen or straight-chain or branched alkyl having up to 6 carbon atoms or benzyl, E denotes an oxygen or sulphur atom, or denotes a group of the formula —NR$^{10}$, Z denotes a sulphur or oxygen atom or the —CH$_2$— group and R represents a radical of the formula

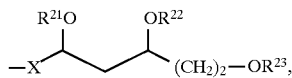

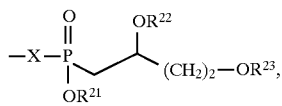

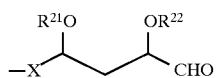

or

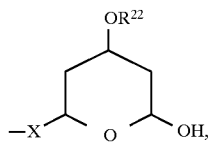

wherein
X denotes the group —CH$_2$—CH$_2$—, —CH=CH— or —C≡C—, $R^{21}$, $R^{22}$ and $R^{23}$ are identical or different and denote a hydroxyl protective group, hydrogen or a radical of the formula —CO—R$^{24}$ or —CO$_2$—R$^{25}$, wherein
$R^{24}$ and $R^{25}$ are identical or different, denote straight-chain or branched alkyl having up to 6 carbon atoms or phenyl, or $R^{21}$ and $R^{22}$ together form a radical of the formula

and their salts

Particularly preferred compounds of the general formula (I) are those in which

D represents a hetero- or carbocyclic radical of the formula

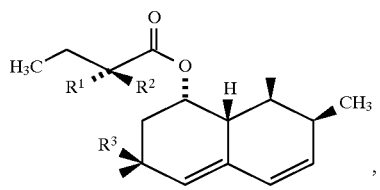

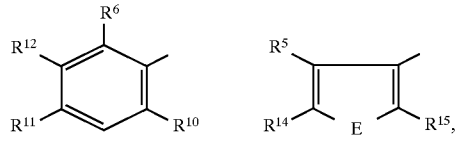

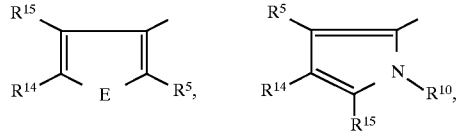

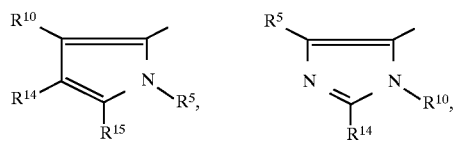

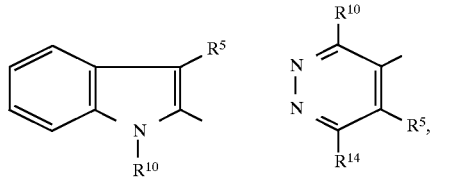

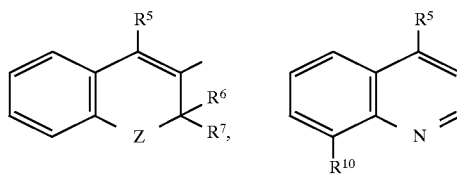

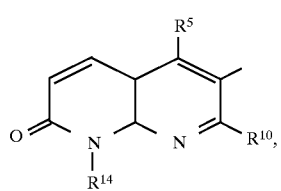

-continued

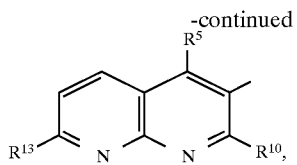

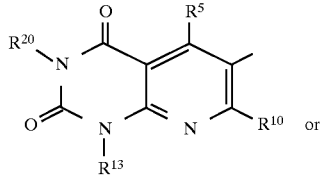

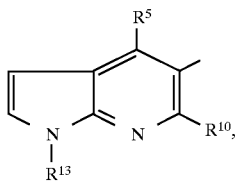

wherein
$R^1$, $R^2$, $R^3$ and $R^4$ are identical or different and denote hydrogen or methyl, or $R^4$ denotes hydroxyl,
$R^5$ denotes phenyl which is optionally substituted by fluorine or trifluoromethyl or by straight-chain or branched alkyl having up to 4 carbon atoms,
$R^6$, and $R^7$ are identical or different and denote hydrogen, straight-chain or branched alkyl having up to 4 carbon atoms or cyclopropyl, or in each case $R^6$ and $R^7$ together form a cyclopropyl or cyclopentyl ring,
$R^{10}$ denotes cyclopropyl or straight-chain or branched alkyl having up to 4 carbon atoms,
$R^{11}$ has the abovementioned meaning of $R^{10}$ and is identical to or different from this or denotes hydrogen,
$R^{12}$ denotes hydrogen or for straight-chain or branched alkyl having up to 4 carbon atoms, which is optionally substituted by benzoyl which for its part can be substituted by fluorine,
$R^{14}$ and $R^{15}$ are identical or different and denote hydrogen or straight-chain or branched alkyl having up to 4 carbon atoms, or denote phenyl or benzyl, each of which is optionally substituted by fluorine, trifluoromethyl or straight-chain or branched alkyl having up to 3 carbon atoms
$R^{18}$ denotes hydrogen or straight-chain or branched alkenyl, alkinyl or alkyl having up to 4 carbon atoms, the latter optionally being substituted by cyano or phenyl, which for its part is substituted by fluorine or methyl,
$R^{19}$ denotes straight-chain or branched alkoxy having up to 4 carbon atoms, benzoyl or the group —NMM', wherein
  M and M' are identical or different and denote hydrogen, methyl or benzyl,
$R^{20}$ denotes hydrogen, straight-chain or branched alkyl having up to 4 carbon atoms or benzyl,
E denotes an oxygen or sulphur atom, or denotes a group of the formula —$NR^{10}$,
Z denotes a sulphur or oxygen atom or the —$CH_2$— group and
  R represents a radical of the formula

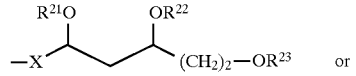

-continued

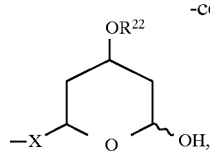

wherein
X denotes the group —CH=CH—,
$R^{21}$, $R^{22}$ and $R^{23}$ are identical or different and denote hydrogen or a radical of the formula —CO—$R^{24}$, wherein
  $R^{24}$ denotes straight-chain or branched alkyl having up to 4 carbon atoms, and their salts.

Particularly preferred compounds of the formula (I) are those in which

D represents a hetero- or carbocyclic radical of the formula

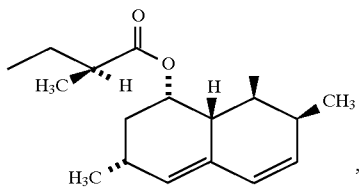

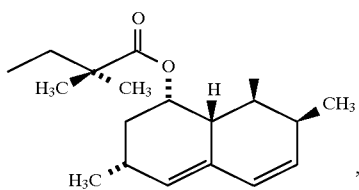

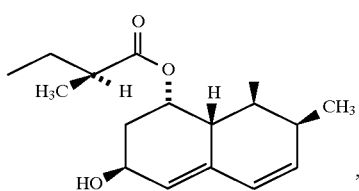

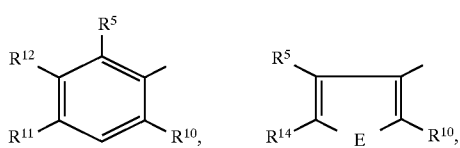

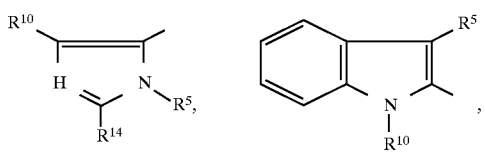

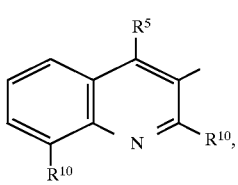

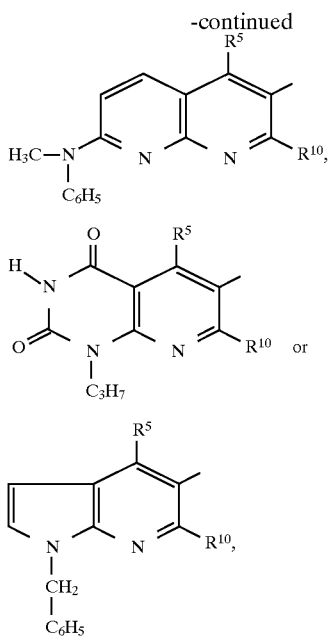

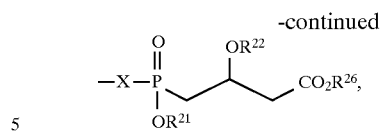

wherein
X, $R^{21}$, $R^{22}$ and $R^{23}$ have the abovementioned meaning and $R^{26}$ represents $C_1$—$C_6$-alkyl,
are reduced with reducing agents in inert solvents, under a protective gas atmosphere, optionally via the stage of the aldehyde,
and in the case where X represents the —$CH_2$—$CH_2$— group, the ethene group (X=—CH=CH—) or the ethine group (X=—C≡C—) is successively hydrogenated according to customary methods, and the isomers are optionally separated.

The process according to the invention can be illustrated by way of example by the following reaction scheme:

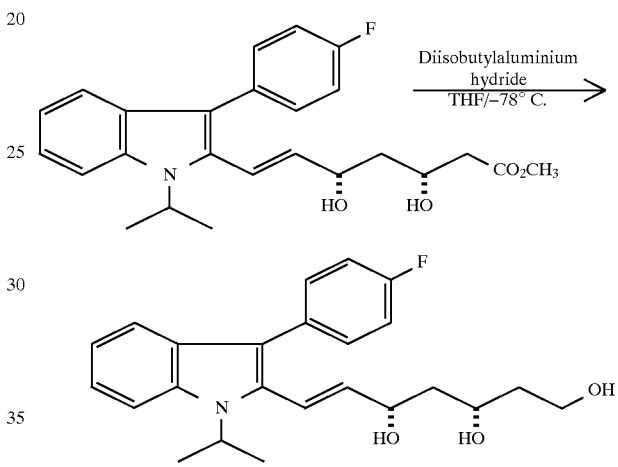

wherein
$R^5$ denotes phenyl which is optionally substituted by fluorine or methyl,
$R^{10}$ denotes cyclopropyl or straight-chain or branched alkyl having up to 3 carbon atoms,
$R^{12}$ denotes hydrogen,
$R^{14}$ denotes phenyl, and
E denotes an oxygen or sulphur atom or denotes a group $NR^{10}$, and
R represents a radical of the formula

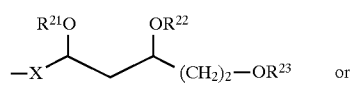

wherein X denotes the group
—CH=CH—,
and $R^{21}$, $R^{22}$ and $R^{23}$ denote hydrogen

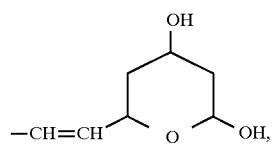

wherein X denotes the group —CH=CH—, and $R^{21}$, $R^{22}$ and $R^{23}$ denote hydrogen and their salts.

A process for the preparation of the compounds of the general formula (I) according to the invention has additionally been found, characterized in that compounds of the general formula (II)

D-T        (II)

in which
D has the abovementioned meaning and
T represents a radical of the formula

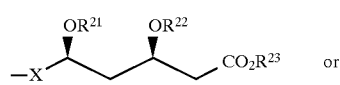

In general, suitable solvents for the reduction are organic solvents. Ethers such as diethyl ether, tetrahydrofuran or dioxane are preferred. Tetrahydrofuran is preferred.

Suitable reducing agents are metal hydrides, such as, for example, lithium aluminium hydride, sodium cyanoborohydride, sodium aluminium hydride, diisobutylaluminium hydride or sodium bis-(2-methoxyethoxy) dihydroaluminate. Diisobutylaluminium hydride is preferred.

In general, the reducing agent is employed in an amount from 4 mol to 10 mol, preferably from 4 mol to 5 mol, relative to 1 mol of the compounds of the general formula (II).

In general, the reduction proceeds in a temperature range from −78° C. to +100° C., preferably from −78° C. to 0° C., particularly preferably at −78° C., in each case depending on the choice of the reducing agent.

The reduction in general proceeds at normal pressure, but it is also possible to work at elevated or reduced pressure.

The cyclization of the aldehydes to the corresponding pyrans is in general carried out at room temperature or by heating in inert organic solvents, optionally in the presence of molecular sieve.

Suitable solvents in this case are hydrocarbons such as benzene, toluene, xylene, petroleum fractions, or tetralin or diglyme or triglyme. Benzene, toluene or xylene are preferably employed. It is also possible to employ mixtures of the solvents mentioned. Hydrocarbons, in particular toluene, in the presence of molecular sieve are particularly preferably used.

The cyclization is in general carried out in a temperature range from −40° C. to +200° C., preferably from −25° C. to +50° C.

The hydrogenation is carried out by customary methods using hydrogen in the presence of noble metal catalysts, such as, for example, Pd/C, Pt/C or Raney nickel in one of the abovementioned solvents, preferably in alcohols such as, for example, methanol, ethanol or propanol, in a temperature range from −20° C. to +100° C., preferably from 0° C. to +50° C., at normal pressure or elevated pressure.

The reduction of the triple or double bond is optionally also carried out during the abovementioned reduction of the ester group.

The compounds of the general formula (II) are known or can be prepared by customary methods.

In the case of the enantiomerically pure compounds of the general formula (I), either the corresponding enantiomerically pure esters of the general formula (II) are employed which are obtained by published processes by reaction of the racemic products with enantiomerically pure amines to give the corresponding diastereomeric amide mixtures, subsequent separation by chromatography or crystallization into the individual diastereoisomers and subsequent hydrolysis [cf. DOS (German Published Specification) 40 40 026] or in that the racemic final products are separated by customary chromatographic methods.

The substituted hetero- and carbocyclic triols according to the invention and also their isomeric forms have useful pharmacological properties which are superior in comparison to the prior art, in particular they are highly active inhibitors of 3-hydroxy-3-methyl-glutaryl coenzyme A (HGM-CoA) reductase and as a result of this inhibitors of cholesterol biosynthesis. They can therefore be employed for the treatment of hyperlipoproteinaemia or arteriosclerosis. The active substances according to the invention additionally effect a reduction of the cholesterol content in the blood.

The pharmacological action of the substances according to the invention was determined in the following test:

Biological test for HMG-CoA Lactase inhibitors

Cholesterol is synthesized from acetate units in the mammalian body. In order to measure hepatic cholesterol biosynthesis in vivo, radiolabelled $^{14}$C-acetate was administered to the animals and the content of $^{14}$C-cholesterol was later determined in the liver.

The substances to be investigated were tested for inhibition of hepatic cholesterol biosynthesis in vivo in male Wistar rats having a body weight of between 140 and 160 g. For this purpose, the rats were weighed 18 hours before oral administration of the substances, divided into groups of 6 animals (control group without substance loading 8 animals) and fasted. The substances to be investigated were suspended in aqueous 0.75% strength tragacanth suspension using an Ultra-Turrax directly before administration. The tragacanth suspension (control animals) or the substances suspended in tragacanth were administered by means of a stomach tube. 2 hours oral administration of substance, $^{14}$C-acetate (12.5 $\mu$Ci/animal) was injected into the animals intraperitoneally.

A further 2 hours later (4 hours after administration of substance), the animals were sacrificed by cutting the throat and exsanguinated. The abdomen was then opened and a liver sample of about 700 mg was taken for the determination out of $^{14}$C-cholesterol. The cholesterol was extracted in a modified manner according to Duncan et al. (J. Chromatogr. 162 (1979) 281–292). The liver sample was homogenized in isopropanol in a glass potter. After shaking and subsequent centrifugation, the supernatant was treated with alcoholic KOH and the cholesterol esters hydrolyzed. After hydrolysis, the total cholesterol was extracted by shaking with heptane and the supernatant was evaporated. The residue was taken up in isopropanol, transferred to scintillation tubes and made up with LSC cocktail. The $^{14}$C-cholesterol synthesized from $^{14}$C-acetate in the liver was measured in a liquid scintillation counter. The hepatic $^{14}$C-cholesterol content of the animals only treated with tragacanth was used as a control. The inhibitory activity of the substances is given in % of the synthesized hepatic $^{14}$C-cholesterol content of the tragacanth control animals (=100%).

The present invention also includes phamaceutical preparations which, in addition to inert, non-toxic, pharmaceutically suitable auxiliaries and incipients, contain one or more compounds of the general formula (I), or which consist of one or more active substances of the formula (I), and processes for the production of these preparations.

The active substances of the formula (I) should be present in these preparations in a concentration of 0.1 to 99.5% by weight, preferably of 0.5 to 95% by weight, of the total mixture.

In addition to the active substances of the formula (I), the pharmaceutical preparations can also contain other pharmaceutical active substances.

The abovementioned pharmaceutical preparations can be prepared in a customary manner by known methods, for example using the auxiliary(ies) or excipient(s).

In general, it has proven advantageous to administer the active substance(s) of the formula (I) in total amounts of about 0.1 $\mu$g/kg to about 100 $\mu$g/kg, preferably in total amounts of about 1 $\mu$g/kg to 50 $\mu$g/kg, of body weight every 24 hours, optionally in the form of several individual doses, to achieve the desired result.

However, in some cases it can be advantageous to depart from the amounts mentioned, mainly depending on the species and the body weight of the subject treated, on the individual behaviour towards the medicament, the nature and severity of the disorder, the type of preparation and administration, and the time or interval at which administration takes place.

PREPARATION EXAMPLES

Example 1 erythro(E)-7-[1-Benzyl-4(4-fluorophenyl)-6-isopropyl-1H-pyrrolo[2,3-b]pyridin-5-yl]hept-6-ene-1,3,5-triol

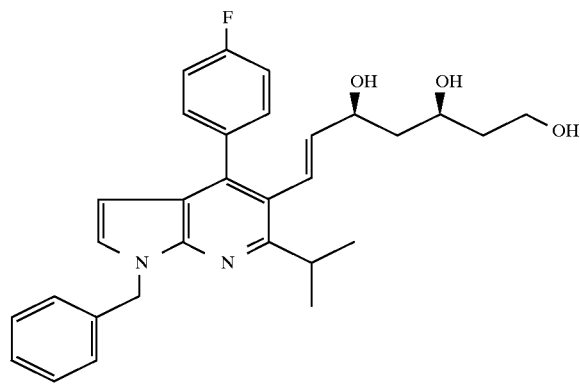

1.33 ml (2 mmol) of a 1.5M diisobutyl-aluminium hydride solution in toluene is added dropwise under argon at −78° C. to a solution of 207 mg (0.4 mmol) of methyl erythro(E)-7-[4-(4-fluorophenyl-6-isopropyl-1H-pyrrolo[2,3-b]pyridin-5-yl]-3,5-dihydroxy-hept-6-enoate in 5 ml of anhydrous THF. The mixture is stirred at −78° C. for 2.5 h, allowed to stand at −30° C. for 16 h, then, after removing the cooling, treated cautiously with 5 ml of water and 2 ml of 1N hydrochloric acid and extracted with ethyl acetate. The colloidal precipitate is filtered off with suction through kieselguhr and the organic phase is washed with satd saline solution, dried over sodium sulphate and concentrated. After chromatography in 15 g of silica gel (230–400 mesh) using methylene chloride/ethyl acetate (1:2), 47 mg (38%) of a colourless oil are obtained. FAB-MS: 489 (100%, M+H)

The following were prepared analogously:

Example 2

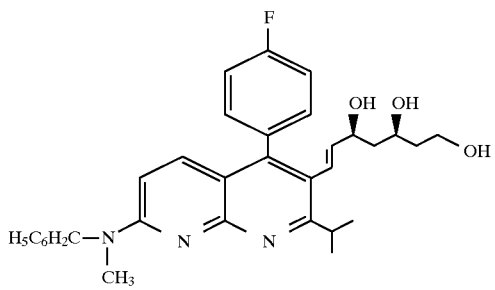

Yield: 43% amorphous

MS data: 530 (79%, M+1) FAB

Example 3

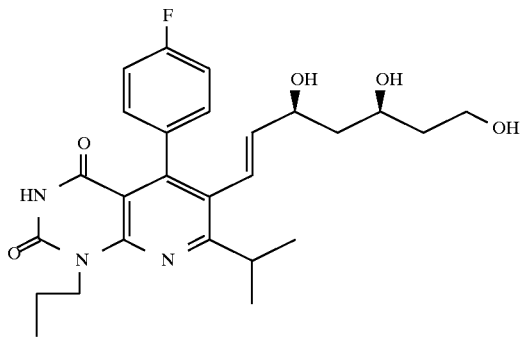

Yield: 31% amorphous

MS data: 486 (100%, M+1) DCI

Example 4

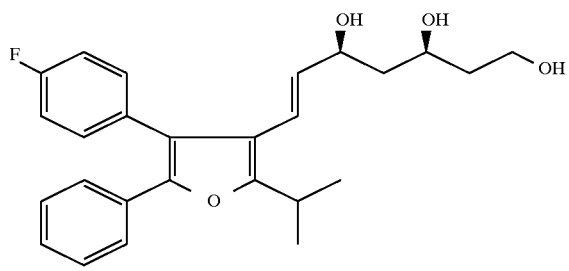

Yield: 24%

M.p.: 119° C.

MS data: 424 β 5%, M+) DCI

Example 5

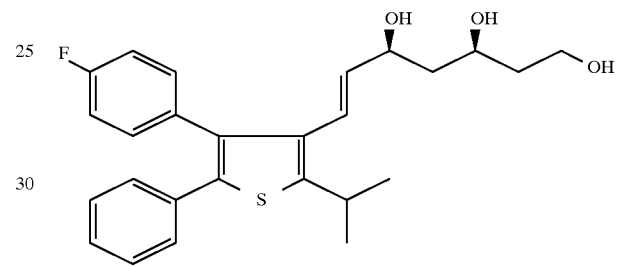

Yield: 30%

M.p.: 114° C.

MS data: 440 (25%, M+) DCI

Example 6

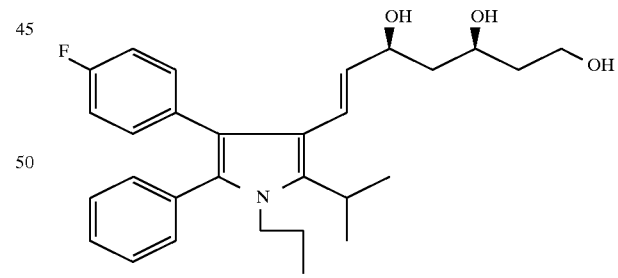

Yield: 26% amorphous

MS data: 465 (60%, M+)FAB

Example 7 erythro-(E)-7-[2-Cyclopropyl-4-(4-fluorophenyl)-8-methyl-quinolin-3-yl]-hept-6-ene-1,3,5-triol

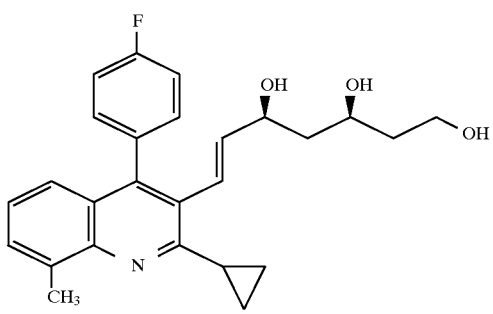

225 mg (0.5 mmol) of methyl erythro-(E)-7-[2-cyclopropyl-4-(4-fluorophenyl)-8-methyl-quinolin-3-yl]-3,5-dihydroxy-hept-6-enoate are dissolved in 20 ml of absol. tetrahydrofuran and, after addition of 76 mg (2 mmol) of sodium borohydride, the mixture is boiled under reflux for 4 h. After cooling the reaction solution, 10 ml of saturated ammonium chloride solution and 10 ml of H$_2$O are added and it is then extracted 3 times with 50 ml of ethyl acetate each time. The organic phase is washed with saturated NaCl solution, dried with Na$_2$SO$_4$ and concentrated on a rotary evaporator. After chromatography on silica gel 60 (25–40 μ, eluent: ethyl acetate/petroleum ether 8/2), the desired product is obtained.

Yield: 73 mg (35% of theory), M.p. 148° C.
FAB-MS: 422 (100%, M+H)

Example 8

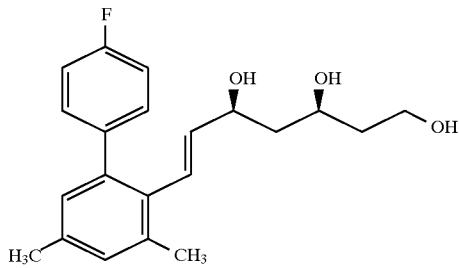

Yield: 63%
amorphous
MS data: (25%, M+) FAB

Example 9

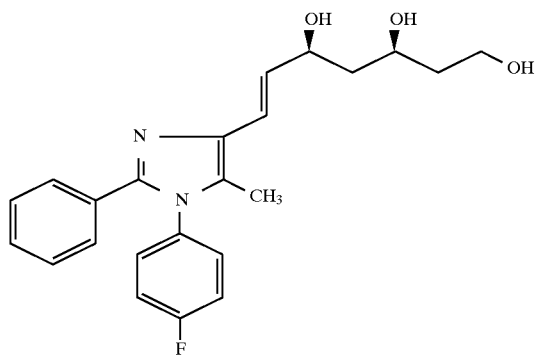

Yield: 71%
amorphous
MS data: (100%, M+1) FAB

Example 10

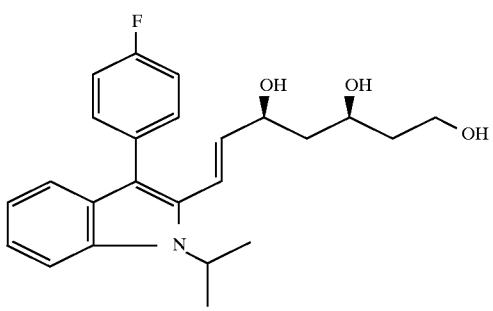

Yield: 60%
amorphous
MS data (100%, M+)FAB

Example 11

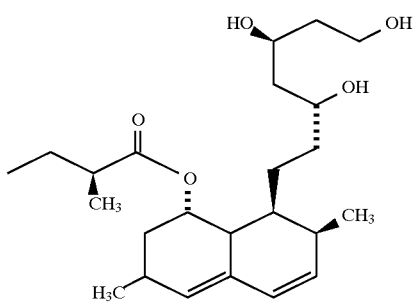

Yield: 49%
amorphous
MS data: (100%, M+1) DCI

Example 12

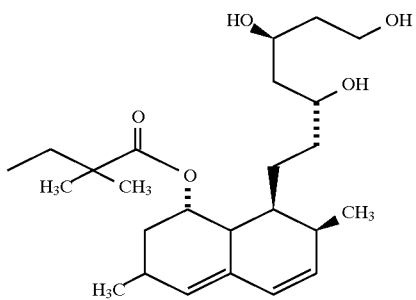

Yield: 19%
amorphous
MS data (100%, M+1) DCI

We claim:
1. Substituted triols of the general formula

$$D-R \qquad (I)$$

in which

D represents a carbocyclic radical of the formula

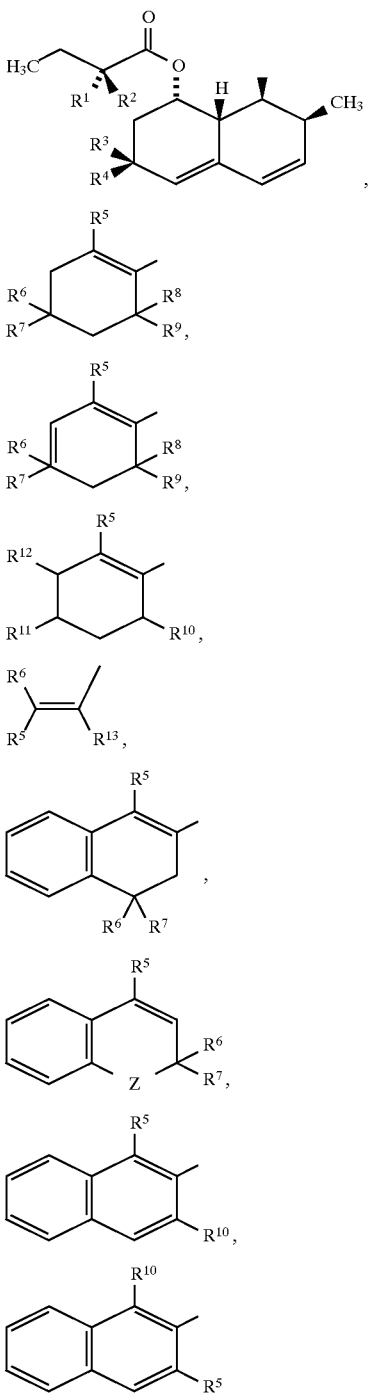

wherein
R$^1$, R$^2$, R$^3$ and R$^4$ are identical or different and denote hydrogen or methyl, or R$^4$ denotes hydroxyl,
R$^5$ denotes phenyl which is unsubstituted or substituted up to 2 times by identical or different substituents from the group consisting of halogen, trifluoromethyl and straight-chain or branched alkyl having up to 8 carbon atoms,
R$^6$, R$^7$, R$^8$ and R$^9$ are identical or different and denote hydrogen, straight-chain or branched alkyl having up to 8 carbon atoms or cycloalkyl having 3 to 6 carbon atoms, or in each case R$^6$ and R$^7$ and/or in each case R$^8$ and R$^9$ together form a saturated or partially unsaturated carbocycle having 3 to 6 carbon atoms
R$^{10}$ denotes cycloalkyl having 3 to 7 carbon atoms, or denotes straight-chain or branched alkyl having up to 8 carbon atoms,
R$^{11}$ denotes hydrogen, phenyl, cycloalkyl having 3 to 7 carbon atoms, or denotes straight-chain or branched alkyl having up to 8 carbon atoms,
R$^{12}$ denotes hydrogen or straight-chain or branched alkyl having up to 8 carbon atoms, which is unsubstituted or substituted by hydroxyl or straight-chain or branched alkoxy having up to 6 carbon atoms, or by benzoyl which benzoyl can be substituted by halogen or trifluoromethyl or by straight-chain or branched alkyl having up to 4 carbon atoms,
R$^{13}$ is hydrogen or straight-chain or branched alkyl having up to 8 carbon
z denotes a —CH$_2$— group and
R represents a radical of the formula

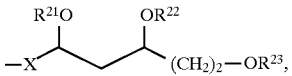

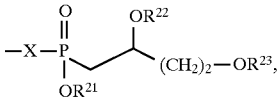

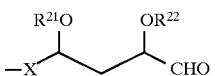

or

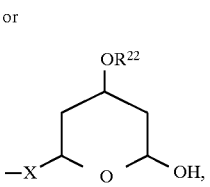

wherein
X denotes the group —CH$_2$—CH$_2$—, —CH=CH— or —C≡C—,
R$^{21}$, R$^{22}$ and R$^{23}$ are identical or different and denote a hydroxyl protective group, hydrogen or a radical of the formula —CO—R$^{24}$ or —CO$_2$—R$^{25}$,
wherein
R$^{24}$ and R$^{25}$ are identical or different and denote straight-chain or branched alkyl having up to 8 carbon atoms or phenyl,
R$^{21}$ and R$^{22}$ together form a radical of the formula

or as a salt thereof with the proviso that when R$^5$ is halogen-substituted tolyl, at least one of R$^{10}$ and R$^{11}$ is other than methyl or ethyl and with the proviso that when D is a partially saturated bicyclic group X is other than a —CH$_2$CH$_2$— group.

2. Substituted triols according to claim 1, wherein
R$^5$ denotes phenyl which is unsubstituted or substituted up to 2 times by identical or different substituents from the group consisting of fluorine, chlorine, bromine and trifluoromethyl or by straight-chain or branched alkyl having up to 6 carbon atoms, $R^6$, $R^7$, $R^8$ and $R^9$ are identical or different and denote hydrogen or straight-chain or branched alkyl having up to 6 carbon atoms or cyclopropyl, cyclopentyl or cyclohexyl,
  or in each case $R^6$ and $R^7$ and/or $R^8$ and $R^9$ together form a cyclopropyl, cyclopentyl or cyclohexyl ring and/or $R^8$ and $R^9$ together form a cyclopentenyl or cyclohexenyl ring, $R^{10}$ denotes cyclopropyl, cyclopentyl or cyclohexyl, or denotes straight-chain or branched alkyl having up to 6 carbon atoms, $R^{11}$ has the abovementioned meaning of $R^{10}$ and is identical to or different from his or denotes hydrogen, $R^{12}$ denotes hydrogen or straight-chain or branched alkyl having up to 6 carbon atoms, which is unsubstituted or substituted by hydroxyl or straight-chain or branched alkoxy having up to 4 carbon atoms, or by benzoyl which benzoyl can be substituted by fluorine, chlorine, bromine, trifluoromethyl or methyl, $R^{13}$ denotes straight-chain or branched alkyl having up to 6 carbon atoms $R^{24}$ and $R^{25}$ are identical or different and denote straight-chain or branched alkyl having up to 6 carbon atoms or phenyl, or $R^{21}$ and $R^{22}$ together form a radical of the formula

and their salts.

3. Substituted triols according to claim 1, where D represents a carbocyclic radical of the formula

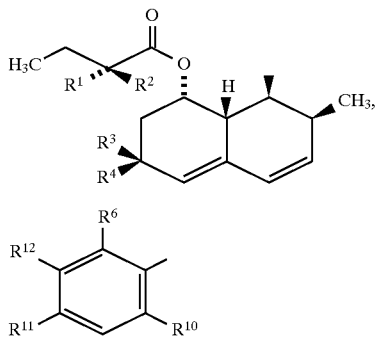

wherein
  $R^1$, $R^2$, $R^3$ and $R^4$ are identical or different and denote hydrogen or methyl, or $R^4$ denotes hydroxyl,
  $R^5$ denotes phenyl which is unsubstituted or substituted by fluorine or trifluoromethyl or by straight-chain or branched alkyl having up to 4 carbon atoms,
  $R^{10}$ denotes cyclopropyl or for straight-chain or branched alkyl having up to 4 carbon atoms,
  $R^{11}$ has the abovementioned meaning of $R^{10}$ and is identical to or different from this or denotes hydrogen,
  $R^{12}$ denotes hydrogen or straight-chain or branched alkyl having up to 4 carbon atoms, which is unsubstituted or substituted by benzoyl which for its part can be substituted by fluorine, R represents a radical of the formula

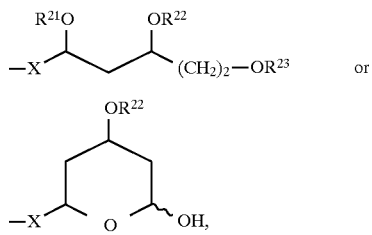

wherein
  X denotes the group —CH=CH—,
  $R^{21}$, $R^{22}$ and $R^{23}$ are identical or different and denote hydrogen or a radical of the formula —CO—$R^{24}$, wherein
  $R^{24}$ denotes straight-chain or branched alkyl having up to 4 carbon atoms,
and their salts.

4. Method for retarding cholesterol biosynthesis and reducing the cholesterol content in the blood which comprises administering an effective amount of a substituted triol according to claim 1.

5. Medicaments for the treatment of excess levels cholesterol in the blood which contain an effective amount of at least one substituted triol according to claim 1.

6. Medicaments for the treatment of hyperlipoproteinaemia which contain an effective amount of at least one substituted triol according to claim 1.

7. Method for the treatment of hyperlipoproteinaemia which comprises administering an effective amount of at least one substituted triol according to claim 3.

8. Process for the preparation of substituted triols according to claim 1, wherein
  compounds of the general formula (II)

$$D-T \qquad\qquad (II)$$

in which
  D has the abovementioned meaning and
  T represents a radical of the formula

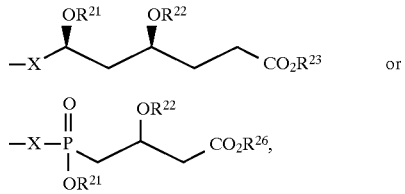

wherein
  X, $R^{21}$, $R^{22}$ and $R^{23}$ have the abovementioned meaning and
  $R^{26}$ represents $C_1$—$C_6$-alkyl,
are reduced with reducing agents in inert solvents, under protective gas atmosphere, optionally via the stage of the aldehyde,
and in the case where X represents the —$CH_2$—$CH_2$— group, the ethene group (X==—CH—CH—) or the ethine (X==—C≡C—) is successively hydrogenated according to customary methods, and the isomers are optionally separated.

* * * * *

UNITED STATES PATENT AND TRADEMARK OFFICE
CERTIFICATE OF CORRECTION

PATENT NO : 5,861,385
DATED : January 19, 1999
INVENTOR(S): Angerbauer, et al.

It is certified that error appears in the above-identified patent and that said Letters Patent is hereby corrected as shown below:

Col. 23, line 20   Delete " 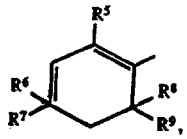 " and substitute

-- 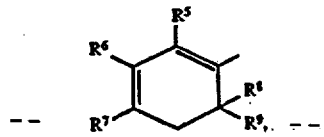, --

Col. 23, line 25   Delete " 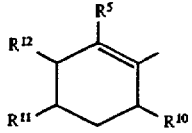 " and substitute

-- 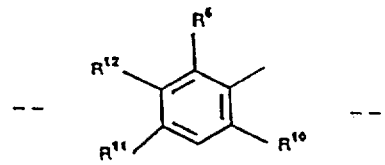 --

Col. 24, line 17   After " 8 carbon " insert -- atoms --

UNITED STATES PATENT AND TRADEMARK OFFICE
CERTIFICATE OF CORRECTION

PATENT NO : 5,861,385
DATED : January 19, 1999
INVENTOR(S): Angerbauer, et al.

It is certified that error appears in the above-identified patent and that said Letters Patent is hereby corrected as shown below:

Col. 25, line 14   Delete " his " and substitute -- this --

Signed and Sealed this

Eighth Day of August, 2000

Attest:

Q. TODD DICKINSON

*Attesting Officer*   *Director of Patents and Trademarks*